(12) United States Patent
Truckai et al.

(10) Patent No.: US 8,562,620 B2
(45) Date of Patent: Oct. 22, 2013

(54) BONE TREATMENT SYSTEMS

(75) Inventors: Csaba Truckai, Saratoga, CA (US);
Andrew Kohm, San Mateo, CA (US);
John Shadduck, Tiburon, CA (US)

(73) Assignee: Dfine, Inc., San Jose, CA (US)

( * ) Notice: Subject to any disclaimer, the term of this patent is extended or adjusted under 35 U.S.C. 154(b) by 641 days.

(21) Appl. No.: 12/427,531

(22) Filed: Apr. 21, 2009

(65) Prior Publication Data

US 2009/0292290 A1 Nov. 26, 2009

Related U.S. Application Data

(60) Provisional application No. 61/124,916, filed on Apr. 21, 2008, provisional application No. 61/104,979, filed on Oct. 13, 2008.

(51) Int. Cl.
*A61B 17/58* (2006.01)

(52) U.S. Cl.
USPC .............................. 606/94; 606/93

(58) Field of Classification Search
USPC ............ 606/92, 93, 94; 604/191, 231, 82–92; 623/23.62
See application file for complete search history.

(56) References Cited

U.S. PATENT DOCUMENTS

| | | | |
|---|---|---|---|
| 3,349,840 A | 10/1967 | Tope et al. | |
| 3,376,999 A | 4/1968 | De Hart et al. | |
| 3,739,947 A | 6/1973 | Baumann et al. | |
| 4,377,168 A | 3/1983 | Rzasa et al. | |
| 5,051,482 A | 9/1991 | Tepic | |
| 5,130,950 A | 7/1992 | Orban et al. | |
| 5,145,250 A | 9/1992 | Planck et al. | |
| 5,531,683 A * | 7/1996 | Kriesel et al. | 604/89 |
| 5,542,928 A | 8/1996 | Evans et al. | |
| 5,688,252 A | 11/1997 | Matsuda et al. | |
| 5,713,857 A | 2/1998 | Grimard et al. | |
| 5,788,711 A | 8/1998 | Lehner et al. | |
| 5,865,798 A | 2/1999 | Grimard et al. | |
| 5,899,881 A * | 5/1999 | Grimard et al. | 604/89 |
| 6,075,067 A | 6/2000 | Lidgren | |
| 6,122,549 A | 9/2000 | Sharkey et al. | |

(Continued)

FOREIGN PATENT DOCUMENTS

WO   WO 02/087416   11/2002

OTHER PUBLICATIONS

Belkoff et al., The Effect of the Monomer-to-Polymer Ratio on the Material Properties of Acrylic Bone Cement, 2002, Wiley Periodicals, Inc. J Biomed Mater Res (Appl Biomater) 63: 396-399, Abstract, accessed Aug. 7, 2012 PubMed.*
U.S. Appl. No. 12/759,573, filed Apr. 13, 2010, Shadduck et al.

*Primary Examiner* — David Isabella
*Assistant Examiner* — Marcia Hoffman
(74) *Attorney, Agent, or Firm* — Knobbe Martens Olson & Bear LLP (57) ABSTRACT

Systems, bone cements and methods for treating vertebral compression fractures can utilize a bone cement comprising of a mixable liquid monomer component and a non-liquid component including polymer particles, wherein the non-liquid component is configured for controlled exposure to the liquid monomer over a setting interval of the bone cement. In a method of use, liquid and non-liquid components are mixed, and the bone cement is injected into bone wherein a lengthened setting interval is provided in which the mixture is configured for a flowability that prevents unwanted extravasation.

24 Claims, 4 Drawing Sheets

(56) References Cited

U.S. PATENT DOCUMENTS

| | | | |
|---|---|---|---|
| 6,264,659 B1 | 7/2001 | Ross et al. | |
| 6,312,149 B1 | 11/2001 | Sjovall et al. | |
| 6,575,930 B1 * | 6/2003 | Trombley et al. | 604/82 |
| 6,709,149 B1 * | 3/2004 | Tepic | 366/139 |
| 6,736,537 B2 | 5/2004 | Coffeen et al. | |
| 6,832,988 B2 | 12/2004 | Sprout | |
| 6,964,667 B2 | 11/2005 | Shaolian et al. | |
| 6,979,352 B2 | 12/2005 | Reynolds | |
| 7,008,433 B2 | 3/2006 | Voellmicke et al. | |
| 7,048,720 B1 | 5/2006 | Thorne, Jr. et al. | |
| 7,048,743 B2 * | 5/2006 | Miller et al. | 606/94 |
| 7,160,020 B2 * | 1/2007 | Sand | 366/139 |
| 7,259,210 B2 * | 8/2007 | Puckett et al. | 525/193 |
| 7,559,932 B2 * | 7/2009 | Truckai et al. | 606/92 |
| 7,678,116 B2 | 3/2010 | Truckai et al. | |
| 2002/0068974 A1 | 6/2002 | Kuslich et al. | |
| 2002/0156483 A1 | 10/2002 | Voellmicke et al. | |
| 2004/0180986 A1 * | 9/2004 | Bellare et al. | 523/115 |
| 2006/0000284 A1 * | 1/2006 | Sherman et al. | 73/645 |
| 2006/0052794 A1 * | 3/2006 | McGill et al. | 606/93 |
| 2006/0079834 A1 | 4/2006 | Tennican et al. | |
| 2008/0188858 A1 * | 8/2008 | Luzzi et al. | 606/94 |
| 2009/0062808 A1 * | 3/2009 | Wolf, II | 606/93 |
| 2009/0093550 A1 * | 4/2009 | Rolfes et al. | 514/772.7 |
| 2009/0171362 A1 * | 7/2009 | Schaeffer | 606/94 |
| 2009/0281549 A1 * | 11/2009 | Dixon | 606/94 |
| 2010/0091606 A1 | 4/2010 | Kwan et al. | |
| 2010/0110436 A1 * | 5/2010 | Chandler et al. | 356/432 |
| 2010/0168271 A1 * | 7/2010 | Beyar et al. | 523/116 |

* cited by examiner

BONE TREATMENT SYSTEMS

CROSS-REFERENCE TO RELATED APPLICATIONS

This application claims the benefit of priority under 35 U.S.C. §119(e) of U.S. Provisional Application Nos. 61/124,916, filed on Apr. 21, 2008, titled Bone System Treatment Systems and Methods and 61/104,979, filed Oct. 13, 2008, titled System for use in Bone Cement Preparation and Delivery. This application is also related to Provisional U.S. Patent Application No. 61/067,480 filed Feb. 28, 2008, titled Bone Treatment Systems and Methods. The entire contents of all of the above applications are hereby incorporated by reference and should be considered a part of this specification.

BACKGROUND OF THE INVENTION

1. Field of the Invention

Embodiments of the present disclosure relate to bone cements and cement injection systems. One embodiment further provides systems and methods for on-demand control of bone cement viscosity for treating vertebral compression fractures and for preventing cement extravasation, wherein a settable bone cement comprises first and second cement precursors that are characterized by a post-mixing working interval in which viscosity changes at a low rate, for example, an extended interval in which the change of viscosity averages less than 50%/minute.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and balloon kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebral body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Balloon kyphoplasty is a modification of percutaneous vertebroplasty which involves a preliminary step of using an inflatable balloon tamp in the vertebral body. Inflation of the balloon creates a cavity in the bone prior to cement injection. In balloon kyphoplasty, the bone cement can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See "Anatomical and Pathological Considerations in Percutaneous Vertebroplasty and Kyphoplasty: A Reappraisal of the Vertebral Venous System," Groen, R. et al., Spine, Vol. 29, No. 13, pp. 1465-1471, 2004. Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al., "The Analysis of Polymethylmethacrylate Leakage after Vertebroplasty for Vertebral Body Compression Fractures," J. of Korean Neurosurg. Soc., Vol. 35, No. 5 (5/2004), pp. 478-82, (http://www.jkns.or.kr/htm/abstract.asp ?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol., 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al., "Asymptomatic Diffuse Pulmonary Embolism Caused by Acrylic Cement: An Unusual Complication of Percutaneous Vertebroplasty," Ann. Rheum. Dis., 2003, 62:85-86. The vapors from PMMA preparation and injection also are cause for concern. See Kirby, B. et al., "Acute Bronchospasm Due to Exposure to Polymethylmethacrylate Vapors During Percutaneous Vertebroplasty," Am. J. Roentgenol, 2003, 180:543-544.

In both higher pressure cement injection (vertebroplasty) and balloon kyphoplasty procedures, the methods do not provide for well controlled augmentation of vertebral body height. The direct injection of bone cement simply follows the path of least resistance within the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a balloon kyphoplasty procedure, the physician often uses very high pressures (e.g., up to 200 or 300 psi) to inflate the balloon which crushes and compacts cancellous bone. Expansion of the balloon under high pressures close to cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.

SUMMARY OF THE INVENTION

There is a general need to provide bone cements and methods for use in treatment of vertebral compression fractures that provide a greater degree of control over introduction of cement and that provide better outcomes. The present invention meets this need and provides several other advantages in a novel and nonobvious manner.

Certain embodiments provide bone cement injectors and that allow for vertebroplasty procedures that inject cement having a substantially controlled high viscosity over an extended cement injection interval.

A bone cement syringe of some embodiments is provided that carries a plurality of curable bone cement portions that each have a different time-viscosity curve for injection within different serial injection intervals over the duration of a procedure, and the cement also can include differing amounts of other non-curable materials intermixed with the bone cement.

Some embodiments of a method of controlling the viscosity of a bone cement over a treatment interval comprise wetting or saturating a column of biomaterial to initiate a curing process and to create a column of curable bone cement and injecting the column of a bone cement into a bone. The different portions of the column of bone cement can have different pre-selected time-viscosity characteristics.

In some embodiments of the above methods, the column of biomaterial can comprise a column of a non-liquid component of the bone cement and the step of wetting can be performed with a liquid component of the bone cement. The column of the non-liquid component can also comprise different portions with each portion configured to provide the column of bone cement with the different portions having different pre-selected time-viscosity characteristics.

The step of injecting of certain methods can further comprise injecting the bone cement into the bone while the bone cement is within a pre-selected viscosity range such that each of the different portions is injected while within the range. The different portions can comprise first, second and third portions, wherein when the first portion is within the higher end of the pre-selected viscosity range the second portion is within the lower end of the range and when the second portion is within the higher end of the range the first portion is above the range and the third portion is within the lower end of the range.

Certain embodiments of a method of treating bone with a biomaterial can comprise placing a column of biomaterial in an interior space of an injector body, wherein the column includes a plurality of predetermined column portions comprising different biomaterials, at least one portion comprising a non-liquid polymer component of a curable bone cement, saturating the column with a liquid monomer component of the curable bone cement thereby initiating a curing reaction of the polymer and monomer components, and injecting the column of biomaterial into bone.

In some embodiments of the method the pre-determined column portions include a plurality of different formulations of non-liquid polymer component that following saturation with the monomer component provide each portion with a different predetermined time-viscosity characteristic. Certain methods also can comprise, wherein the saturating step includes applying negative pressure to a first end of the interior space to thereby draw the liquid monomer through the column of biomaterial from a second end of the interior space.

Some embodiments of a biomaterial injection system comprise an elongate structure with an interior space containing a column of biomaterial, wherein the column includes a plurality of predetermined column portions comprising different biomaterials, at least one portion comprising a non-liquid polymer component of a curable bone cement and a mechanism for coupling a negative pressure source to a first end of the interior space to draw a liquid monomer component into the interior space to saturate the polymer component.

The biomaterial injection system of certain embodiments further comprises a funnel member configured for coupling to the elongate structure for receiving the liquid monomer component and/or a force-application system configured for coupling to the elongate structure for pushing the column of biomaterial from the structure.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like FIG. 1 is a perspective view of one embodiment of a bone cement preparation and/or injection system.

DETAILED DESCRIPTION OF THE PREFERRED EMBODIMENT

For purposes of understanding the principles of the invention, reference will now be made to the embodiments illustrated in the drawings and accompanying text that describe the invention. As background, in some embodiments, a vertebroplasty procedure using the invention could introduce the injector of FIG. 1 through a pedicle of a vertebra, or in a parapedicular approach, for accessing the osteoporotic cancellous bone. The initial aspects of the procedure can be similar to a conventional percutaneous vertebroplasty wherein the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician can use a scalpel to make a 1 to 5 mm skin incision over each targeted pedicle. Thereafter, the bone cement injector can be advanced through the pedicle into the anterior region of the vertebral body, which typically is the region of greatest compression and fracture. The physician can confirm the introducer path posterior to the pedicle, through the pedicle and within the vertebral body by anteroposterior and lateral X-Ray projection fluoroscopic views or by other methods. The introduction of infill material as described below can be imaged several times, or continuously, during the treatment depending on the imaging method.

DEFINITIONS

"Bone cement, bone fill or fill material, infill material or composition" includes its ordinary meaning and is defined as any material for infilling a bone that includes an in-situ hardenable or settable cement, or a composition that can be infused with such a hardenable cement. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

"Substantially" or "substantial" mean largely but not entirely. For example, substantially may mean about 50% to about 99.999%, about 80% to about 99.999% or about 90% to about 99.999%.

"Vertebroplasty" includes its ordinary meaning and means any procedure wherein fill material is delivered into the interior of a vertebra.

"Osteoplasty" includes its ordinary meaning and means any procedure wherein fill material is delivered into the interior of a bone.

Figure 1:
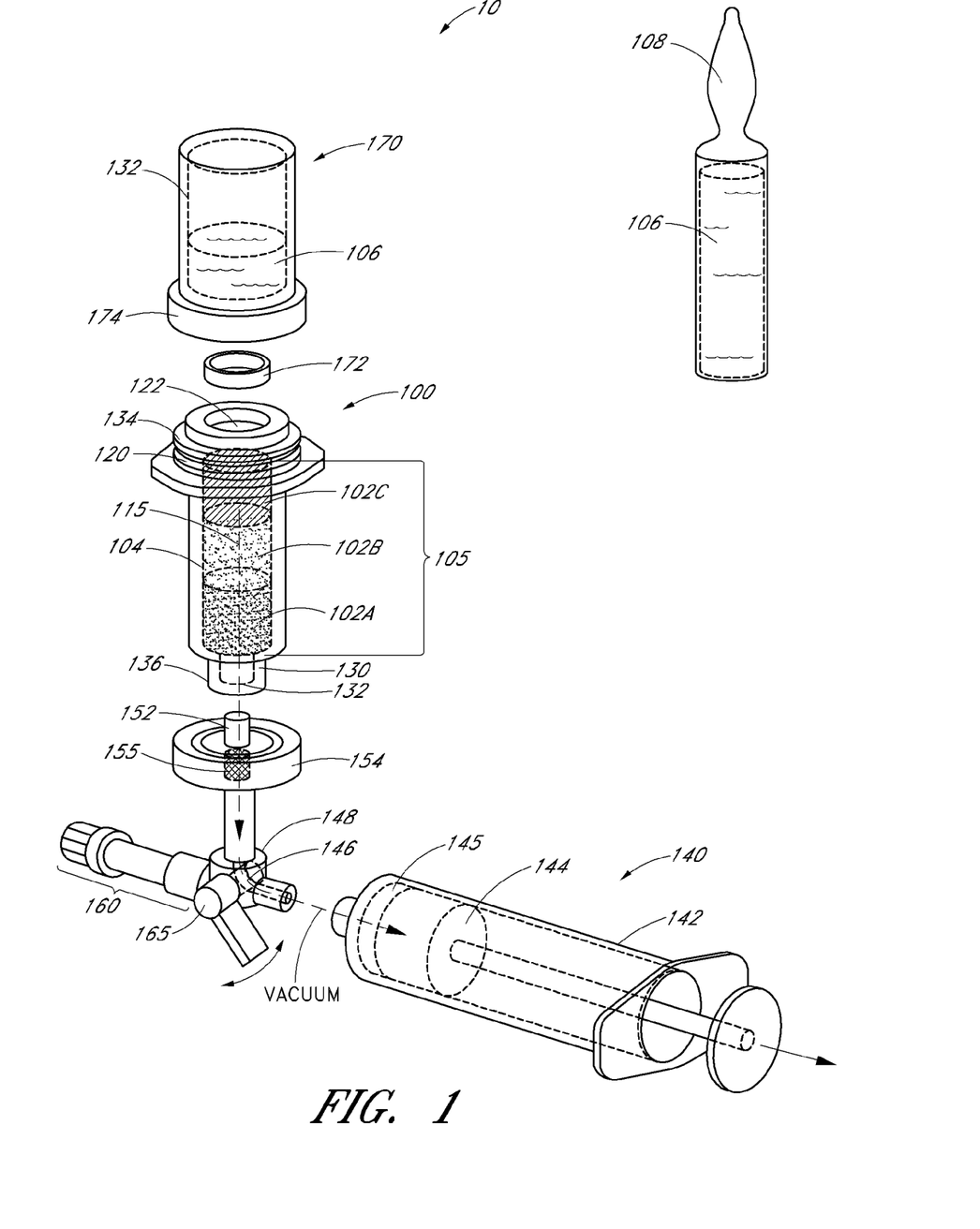

In FIG. 1, a system 10 is illustrated that is adapted for bone cement preparation and thereafter for cement injection in an osteoplasty or vertebroplasty procedure. As can be seen in FIG. 1, a syringe or injector body 100 carries a plurality of different biomaterial formulations 102A, 102B and 102C, each in different axial portions of a biomaterial column in interior chamber 104 of the injector body 100. In one example, body 100 carries three different specialized formulations of the non-liquid polymer powder component 105 of a two-part curable bone cement, such as a PMMA bone cement. As will be described below, the non-liquid component 105 is configured to be wetted or saturated with a liquid monomer component 106 (typically carried in vial 108 pre-mixing) wherein the polymer and monomer components in a post-saturation interval will result in a curable bone cement described further below. However, in other embodiments, the body 100 can carry more or fewer than three different specialized formulations of the non-liquid polymer powder component 105 (e.g., two formulations, four formulations, etc.).

The terms wetting and saturating are used interchangeably herein to describe the process of thoroughly or completely exposing the non-liquid polymer powder component to the liquid monomer component, in other words to unite the two components to thereafter cause a polymerization reaction between at least two portions of the biomaterials. Of particular interest, each of the different polymer formulations 102A, 102B and 102C will result post-mixing in the different time-viscosity curves A, B, C of FIGS. 2A, 2B and 2C, respectively. Each of the PMMA cements 101, 102 and 103 have a different time-viscosity curve indicated at A, B and C. Such different time-viscosity curves as shown can be provided by bone cement formulations that for example, vary the levels of initiator and activator, as well as varying the mean dimensions of the polymer particles. Tecres S. P. A., Via A. Doria, 6 Sommacampagna, Verona, Italy is a bone cement manufacturing company that has the expertise to formulate PMMA bone cements with the various time-viscosity profiles described above.

Referring to FIG. 1, one embodiment of system 10 includes an elongated cement or biomaterial-carrying body 100, which can be of a transparent plastic and can carry a pre-packed volume of non-liquid polymer powder components, indicated collectively at 105. The body 100 extends along an axis 115 from a proximal end 120 with opening 122 into the interior space 104 to a distal end 130 with an open termination 132 of the interior space 104. The proximal end 120 of the cement-carrying body 100 can have a fitting such as, for example, a threaded fitting 134 for connecting a pressurization mechanism to the structure. The distal end 130 of the structure 100 can also have a fitting 136 (e.g., a Luer fitting) for connecting a filter and vacuum source to the body as will be described further below.

Still referring to FIG. 1, the biomaterial-carrying body 100 has an elongate configuration with a cross-section of the interior space 104 having a diameter between about 2 mm and 20 mm. The length of body 100 can range from about 5 cm to 20 cm, to provide an interior volume of from about 2 cc to 20 cc. In one embodiment, the body 100 is transparent to thus allow viewing of monomer saturation described below. In use in a vertebroplasty procedure, one or more biomaterial-carrying bodies 100 can be used, as a treatment of a vertebral compression fracture can use from about 2 cc to 8 cc of bone cement. In other embodiments, the biomaterial-carrying body 100 can have other length and diameter dimensions to provide other desired interior volumes for the body 100.

As also can be seen in FIG. 1, the system can include a negative pressure source or assembly 140 that can be detachably coupled to body 100 for suctioning the liquid monomer component 106 into and through the non-liquid polymer powder component 105 disposed in space 104 in the body 100. The saturation of the polymer powder 105 with the monomer 106 thus causes the biomaterial column to begin polymerization and set in post-mixing (or post-saturation) time intervals that are described further below.

In one embodiment, the negative pressure source 140 can comprise a syringe 142 with a lockable plunger assembly 144 slidable within the syringe 142 that can be withdrawn to apply suction from syringe chamber 145 through channel 146 in body 148 that communicates with open termination 132 in body 100 when connected together by cooperating fittings, such as Luer threads 136 of body 100 and the fitting 152 of the negative pressure source or assembly 140.

In another aspect, a structure 154 carrying a filter 155 can be fixedly or detachably connected to body 148 intermediate the biomaterial-carrying body 100 and the negative pressure source 140. The filter 155 can in one embodiment include a plastic (e.g., high density polyethylene) mesh filter having a mean pore dimension of about 0.1 to 0.5 microns and be configured to allow air extraction from the volume of compacted polymer powder in body 100 by initial application of a vacuum from syringe 142, but the liquid monomer component 106 when suctioned through the polymer powder 105 in sleeve 112 creates a higher viscosity mixture akin to a wet sand which will not pass through the filter 155. By this means, the filter 155 can function to limit any liquid monomer losses from the saturated mixture, and can result in a desired (e.g., an exact) volume of liquid monomer 106 being drawn by vacuum into the sleeve for saturating the polymer powder volume 105. As can also be seen in FIG. 1, a pressure relief valve 160 can be provided that limits the amount of negative pressure in the syringe 142.

In some embodiments, the body 148 also carries a valve indicated at 165 for selectively closing channel 146. In use, the valve 165 can be selectively closed, and then the lockable plunger assembly 144 can be withdrawn in chamber 145 and selectively locked, thus providing a selected negative pressure or vacuum in the chamber 145. Thereafter, the liquid monomer 106 can be poured into a funnel 170 (described next), with the body 100 held in a vertical position, and then the valve 165 can be moved to an open position to suction the monomer 106 into and through polymer powder 105 in the body 100.

In another embodiment, an alternative negative pressure source 140 can comprise a canister pre-packaged with a suitable level of vacuum therein. The vacuum canister then can be coupled to a valve and further coupled to the body 148 of FIG. 1 to provide a negative pressure source for saturating the biomaterial column with the liquid monomer.

The system of FIG. 1 can in one embodiment further include a funnel mechanism for assisting the step of pouring the requisite volume of liquid monomer 106 into the open end 122 of the proximal end 120 of body 100. In one embodiment as depicted in FIG. 1, the funnel mechanism comprises a funnel member 170 that is attachable to body 100 wherein the volume of the funnel is sized to contain the selected volume of monomer 106 required to saturate the volume of polymer powder 105 in the biomaterial-carrying body 100. The funnel member 170 can be fabricated of a clear plastic and have a fluid-tight fitting, such as an o-ring 172, to couple to body 100 with threaded portion 174.

The systems for preparing bone cement, of some embodiments, further comprise a cement ejection mechanism coupleable to the body 100 for ejecting the bone cement from the body 100 into bone, wherein a piston or driving shaft is inserted into space 104 to drive the bone cement through a needle (not shown) coupled to the distal end 130 of body 100. The cement ejection mechanism can in one embodiment include a manually advanced plunger assembly, or any type of hydraulic system, CO2 gas cartridge system, pneumatic system, cable drive system, screw drive system, a spring system or other pump system any of which can be computer controlled with a microprocessor that executes one or more control algorithms for delivering the curable bone cement at desired flow parameters (e.g., flow rate, temperature, pressure) into a treatment site (e.g., into naturally-occurring cavities in uncompressed cancellous bone of a bone, such as a vertebral body).

Still referring to FIG. 1, it can be understood that a method is provided for controlling the viscosity of a bone cement over a treatment interval that comprises injecting a column of a bone cement into bone wherein different portions of a column of bone cement have different time-viscosity characteristics. The method can include a plurality of different bone cement portions in a column, for example with the different time-viscosity characteristics, the number of different portions being at least 2, 3, 4, 5 or more. The method can utilize different bone cement portions disposed in axial portions of a column or in concentric portions of a column. The method further comprises controlling the rate of injecting the column of bone cement with a non-manual drive system and controller. The rate of injection (e.g., velocity, acceleration, flow rate or pressure) can be controlled by a manual drive system and a sensor system that provides feedback of the rate of injection by at least one of visual, aural or tactile signals. The rate of injection can be selected to reduce the potential of emboli from entering the vascular system. This can be done with a rate of injection that is less than 2-5 cc per minute. In some embodiments, the rate of injection can be constant, and between 0.1 cc and 5 cc per minute or between 0.5 cc and 2 cc per minute.

Figure 2A:
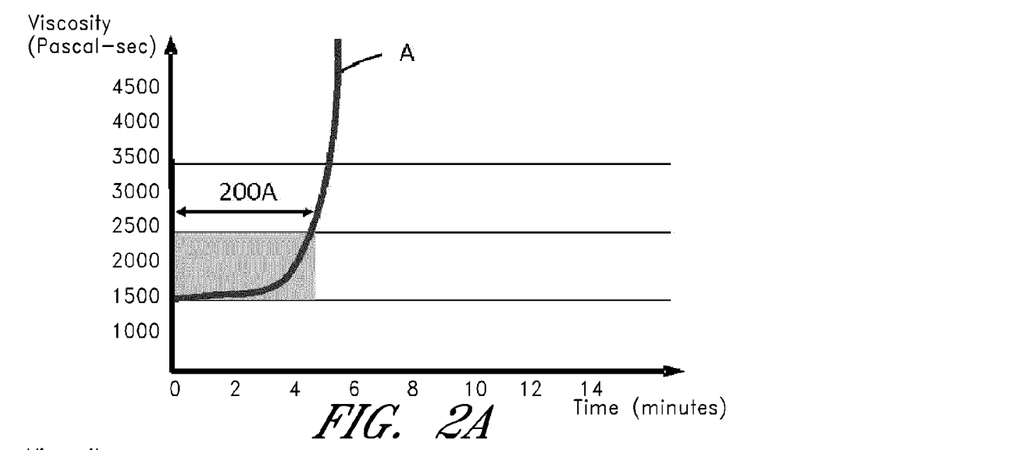
FIG. 2A is a chart indicating a time-viscosity curve for a first curable PMMA bone cement.
Figure 2B:
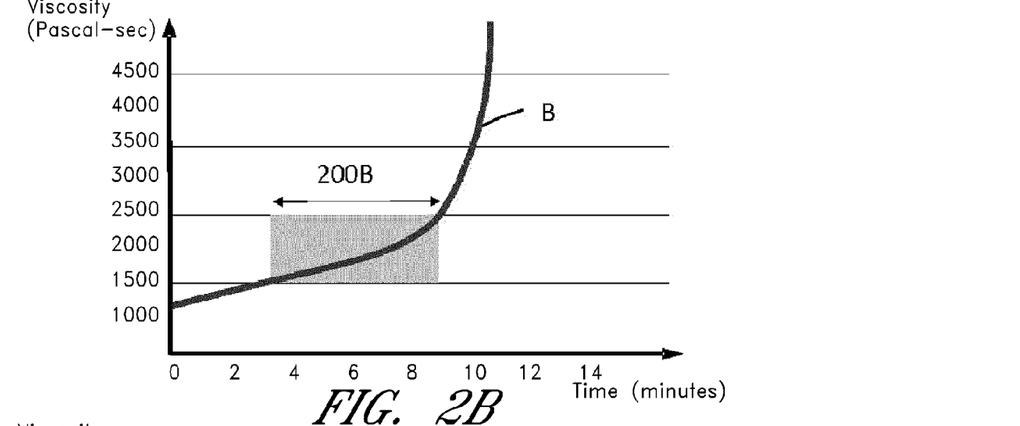
FIG. 2B is a chart indicating a time-viscosity curve for a second curable PMMA bone cement.
Figure 2C:
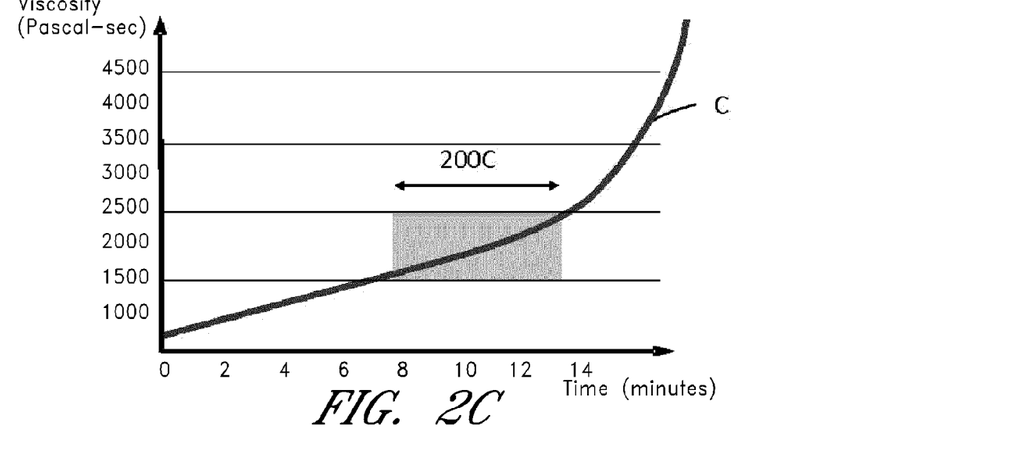
FIG. 2C is a chart indicating a time-viscosity curve for a third curable PMMA bone cement.

Referring to FIGS. 2A-2C and FIG. 3, in one example, it can be understood that the first portion of bone cement have time viscosity curve A (from polymer component 102A of FIG. 1) can be injected first from body 100 into bone over a first time interval of about 4 minutes indicated at 200A in FIG. 2A. As can be seen in FIG. 2A, the cement viscosity in the first time interval 200A is between about 1500 Pa·s and 2500 Pa·s. The injection rate can be controlled so that this initial column of cement is ejected from body 100 during the first time interval and before about the time that the second different portion of cement is injected into bone (from polymer component 102B of FIG. 1). As can be seen in FIG. 2B, for a time interval 200B of 4 or more minutes, the time-viscosity curve B provides a cement having a viscosity again between about 1500 Pa·s and 2500 Pa·s. Now referring to FIG. 2C, the third different column of cement can be injected into bone (from polymer component 102C of FIG. 1). FIG. 2C shows that during time interval 200C, the time-viscosity curve C again provides a cement viscosity between about 1500 Pa·s and 2500 Pa·s, for about four minutes or more. In other embodiments, the different columns of cement can be injected so that the injected bone cement has a different viscosity range than 1500-2500 Pa·s.

Figure 3:
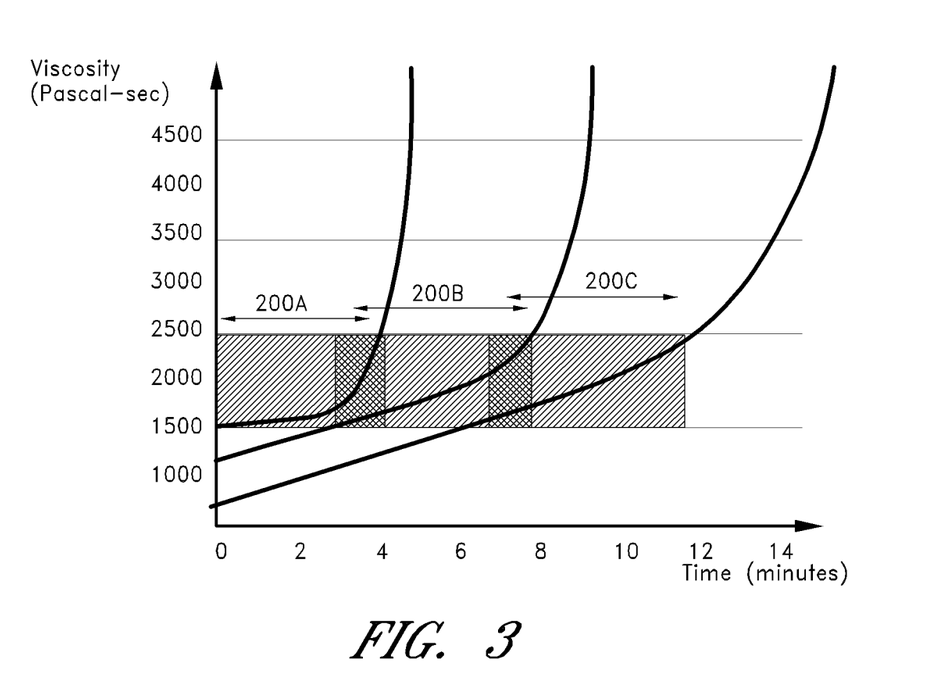
FIG. 3 is a chart illustrating an overlay of the time-viscosity curves of the PMMA bone cements of FIGS. 2A-2C.

Referring now to FIG. 3, it can be seen that the system of FIG. 1 can provide a curable bone cement having a viscosity within a selected range over an extended working time of many minutes, for example at least 8 minutes, 10 minutes, 12 minutes or more by providing a saturation mixing system that pre-packs a column of different cement precursors and biomaterials in a source of bone cement. It should be appreciated that at least one portion of the column of biomaterial can comprise an osteogenic composition, bone chips, or a biodegradable or bioabsorbable material. Thus the bone cement according to some methods can be injected within a set range of viscosity over an extended cement injection interval. Further embodiments can comprise injecting bone cement into bone while the bone cement is within a pre-selected range of viscosity such that each different portion of bone cement is injected while within the range. In some embodiments, the pre-selected range can be about 500 to 4000 Pa·s. In some embodiments, the pre-selected viscosity range is about 1500 to 2500 Pa·s.

In some embodiments, the different portions can comprise first, second and third portions. After the liquid and non-liquid components have been mixed, when the first portion is within the higher end of the pre-selected viscosity range the second portion is within the lower end of the range and when the second portion is within the higher end of the range the first portion is above the range and the third portion is within the lower end of the range.

In another embodiment, a method of treating bone comprises providing an injector containing an axial column of a curable biomaterial, and injecting the column of biomaterial into the interior of a mammalian subject wherein the column has axial non-uniformity in biomaterial curing parameters.

In another embodiment, a method comprises providing an axial column of a curable biomaterial, and injecting the column of biomaterial into a bone wherein the column has a plurality of axial portions characterized by different setting times. The method further comprises injecting at least 3 cc of biomaterial, at least 4 cc of biomaterial, at least 6 cc of biomaterial and at least 8 cc of biomaterial.

In another embodiment, a biomaterial injection system for injecting a curable biomaterial comprises a structure for holding an axially-extending column of a curable biomaterial, a drive system or force-application member for moving the biomaterial from the structure, wherein the column of biomaterial has axial non-uniformity in biomaterial curing parameters. The biomaterial can have non-uniform curing parameters that consist of setting time, time-viscosity curves, change of viscosity over an interval, rate of change of viscosity over an interval, time-temperature curves, and/or the length of an interval between first and second selected viscosities.

In another embodiment, the biomaterial injection system carries a column of curable biomaterial which comprises first and second column portions with first and second curing parameters, respectively. Each column portion can be at least 1 cc, 2 cc, 3 cc, 4 cc, 5 cc, 6 cc, 8 cc and 10 cc. Each column portion can have a different percentage of activator and/or different percentage of initiator. The biomaterial injection system of some embodiments includes a mechanism for introducing a liquid monomer component into the column of biomaterial. A pressurized source of liquid monomer component can be operated at between 0.1 psi and 500 psi. The biomaterial injection system can include a vent in the structure to thereby allow the liquid monomer component to diffuse through the column of biomaterial without backpressure. The biomaterial injection system can have a controller and drive system configured for controllably moving the force-application member to provide a delivery rate of between 0.5 cc and 3 cc per minute.

The system can include a sensor system that provides feedback of the rate of injection by at least one of visual, aural or tactile signals and can include a temperature sensor, flow sensor, electrical parameter sensor, ultrasound sensor, a load cell and a thermochromic material indicator.

In another embodiment, a method of treating bone comprises providing an injector containing an axial column of a non-liquid component of a curable biomaterial, introducing a liquid component of the curable biomaterial into the column of non-liquid component under a selected pressure to allow diffusion of the liquid component within the non-liquid component to thereby initiate a curing reaction without mixing, and injecting the column of biomaterial into the interior of a bone.

In another embodiment, a method of treating bone comprises providing an injector containing an axial column of a non-liquid component of a curable biomaterial, introducing a liquid component of the curable biomaterial into the column of non-liquid component under predetermined parameters allowing for diffusion of the liquid component within the non-liquid component with less than 240 seconds, 120 seconds, 60 seconds, 30 seconds, 20 seconds and 10 seconds. The parameters can include the rate of introducing the liquid component, the pressure of introducing the liquid component, a negative pressure applied to the non-liquid component, and selecting a maximum dimension of any path of diffusion within the non-liquid component. Further, the system may include a mechanism for applying vibratory forces to the injector including ultrasonic vibratory forces. This can further assist in the diffusion of the liquid component into the non-liquid component.

In another embodiment, a combination comprises two settable bone cement formulation that have different time-viscosity curves, wherein said time-viscosity curves are characterized by overlapping time interval of at least 1 minute in the viscosity range of 500 Pa·s to 4000 Pa·s; and a bone cement injector having a chamber for holding the two bone cements formulations. The overlapping time interval is at least 2 minutes, 3 minutes, 4 minutes, 5 minutes and 10 minutes.

Further embodiments relate to bone cement compositions and formulations for use in the bone cement delivery systems described above. The bone cement formulations provide for an extended working time, since the viscosity can be altered and increased on demand when injected.

Bone cements, such as polymethyl methacrylate (PMMA), have been used in orthopedic procedures for several decades, with initial use in the field of anchoring endoprostheses in a bone. For example, skeletal joints such as in the hip are replaced with a prosthetic joint. About one million joint replacement operations are performed each year in the U.S. Frequently, the prosthetic joint is cemented into the bone using an acrylic bone cement such as PMMA. In recent years, bone cements also have been widely used in vertebroplasty procedures wherein the cement is injected into a fractured vertebra to stabilize the fracture and eliminate micromotion that causes pain.

Polymethyl methacrylate bone cement, prior to injection, comprises a powder component and a liquid monomer component. The powder component comprises granules of methyl methacrylate or polymethyl methacrylate, an X-ray contrast agent and a radical initiator. Typically, barium sulfate or zirconium dioxide is used as an X-ray contrast agent. Benzoyl peroxide (BPO) is typically used as the radical initiator. The liquid monomer component typically consists of liquid methyl methacrylate (MMI), an activator, such as N,N-dimethyl-p-toluidine (DMPT) and a stabilizer, such as hydroquinone (HQ). Prior to injecting PMMA bone cements, the powder component and the monomer component are mixed and thereafter the bone cement hardens within several minutes following radical polymerization of the monomer.

Typical bone cements formulations (including PMMA formulations) used for vertebroplasty have a fairly rapid cement curing time after mixing of the powder and liquid components. This allows the physician to not have to waste time waiting for the cement to increase in viscosity prior to injection. Further, the higher viscosity cement is less prone to unwanted extravasation which can cause serious complications. The disadvantage of such current formulations is that the "working time" of the cement is relatively short—for example about 5 to 8 minutes—in which the cement is within a selected viscosity range that allows for reasonably low injection pressures while still being fairly viscous to help limit cement extravasation. In some typical bone cements, the viscosity may range between approximately 50 to 500 Pa·s prior to injection and is measured according to ASTM standard F451, "Standard Specification for Acrylic Bone Cement," which is hereby incorporated by reference in its entirety.

In one embodiment, the bone cement formulation is adapted for use with the cement injectors and energy delivery systems described above. These formulations are distinct from conventional formulations and have greatly extended working times for use in vertebroplasty procedures with the "on-demand" viscosity control methods and apparatus disclosed herein and in co-pending applications listed and incorporated by reference above.

In one embodiment, the bone cement provides a formulation adapted for injection into a patient's body, wherein the setting time is about 25 minutes or more, more preferably about 30 minutes or more, more preferably about 35 minutes or more, and even more preferably about 40 minutes or more. Setting time is measured in accordance with ASTM standard F451.

In one embodiment, the bone cement, prior to mixing and setting, comprises a powder component and a liquid component. The powder component comprises a PMMA that is about 64% to 75% by weight based on overall weight of the powder component. In this formulation, an X-ray contrast medium is about 27% to 32% by weight based on overall weight of the powder component. The X-ray contrast medium, in one embodiment, comprises barium sulfate (BaSO4) or zirconium dioxide (ZrO2). In one embodiment, the formulation further includes BPO that is about 0.4% to 0.8% by weight based on overall weight of the powder component. In another embodiment, the BPO is by weight based on overall weight of the powder component, less than 0.6%, 0.4% and 0.2%. In such formulations, the liquid component can include MMA that is greater than about 99% by weight based on overall weight of the liquid component. In such formulations, the liquid component can include DMPT that is less than about 1% by weight based on overall weight of the liquid component. In such formulations, the liquid component can include hydroquinone that ranges between about 30 and 120 ppm of the liquid component. In such formulations, the liquid weight/powder weight ratio can be equal to or greater than about 0.4. In such formulations, the PMMA can comprise particles having a mean diameter ranging from about 25 microns to 200 microns or ranging from about 50 microns to 100 microns.

In certain embodiments, the concentrations of benzoyl peroxide and DMPT may be varied in order to adjust setting times. Studies examining the influence of bone cement concentration on setting times have demonstrated that, in bone cements comprising BPO and DMPT, increases in BPO and DMPT concentration increase the set time of the bone cement. The data further illustrate that, of the two bone cement constituents, BPO has a greater effect on the rate of set time than does DMPT. Thus, in certain embodiments of the bone cement composition, the concentration of BPO, DMPT, and combinations thereof, may be increased within the ranges discussed above so as to increase the setting time of the composition.

From the forgoing, then, it can be appreciated that by varying the BPO and/or DMPT concentrations of the bone cement composition, the setting time of the bone cement may be increased or decreased. Heating the bone cement composition can also modify the setting time of the bone cement. Furthermore, in certain embodiments, the concentration of BPO and/or DMPT in the bone cement may be varied and the composition may be heated so as to adjust the setting time to a selected value. As discussed above, in certain embodiments, the setting time can be selected to be at least 2 minutes, 4 minutes, 6 minutes, 8 minutes, 10 minutes, 12 minutes or 14 minutes.

In one embodiment, a bone cement has a first component comprising greater than about 99 wt. % methyl methacrylate (MMA), and less than about 1 wt. % N,N-dimethyl-p-toluidine (DMPT), about 30 to 120 ppm hydroquinone on the basis of the total amount of the first component, and a second component comprising a powder component comprising less than 75 wt. % PMMA, less than 32 wt. % of an X-ray contrast medium; and less than 0.4 wt. % benzoyl peroxide (BPO) on the basis of the total weight of the second component. In another embodiment, the second component has less than 0.2 wt. % benzoyl peroxide (BPO) on the basis of the total weight of the second component, or less than 0.1 wt. % benzoyl peroxide (BPO) on the basis of the total weight of the second component. In such a formulation, the liquid weight/powder weight ratio can be equal to or greater than about 0.4. In one embodiment, the PMMA to monomer ratio is 2:1. In another embodiment, the PMMA to monomer ratio is 2.5:1.

In another embodiment, a settable bone cement comprises mixable first and second components, wherein the first component comprises greater than about 99 wt. % methyl methacrylate (MMA), and less than about 1 wt. % N,N-dimethyl-p-toluidine (DMPT), about 30 to 120 ppm hydroquinone on the basis of the total amount of the first component, and wherein the second component comprises a PMMA component comprised of less than 75 wt. % PMMA, less than 32 wt. % of an X-ray contrast medium; and a selected wt. % of benzoyl peroxide (BPO) on the basis of the total weight of the second component. More particularly, the PMMA component includes first and second volumes of beads having first and second amounts of BPO, respectively. In one embodiment, the PMMA component includes a first volume of beads having greater than 0.4 wt. % BPO on the basis of the total weight of the PMMA component and the beads of the first volume have a mean bead size of less than 100 microns. In this embodiment, the PMMA component includes a second volume of beads having less than 0.4 wt. % BPO on the basis of the total weight of the PMMA component and the beads of the second volume have a mean bead size of greater than 100 microns. In another embodiment, the cement has a plurality of different PMMA beads sizes each carrying a different BPO amount, wherein the mean BPO amount among the plurality of beads is from 0.3 to 0.6% BPO on the basis of the total weight.

In another embodiment, the PMMA component includes a first volume of beads greater than 0.4 wt. % BPO on the basis of the total weight of the PMMA and the first volume has a mean bead size of greater than 100 microns. Further, the PMMA component includes a second volume of beads having less than 0.4 wt. % BPO on the basis of the total weight of the PMMA component and the second volume has a mean bead size of less than 100 microns.

In one embodiment, the bone cement comprises a first monomer-carrying component and a second polymer-carrying component, wherein the mixture is characterized by having a viscosity of less than 500 Pa·s at 18 minutes post-mixing. The bone cement further can be characterized as having a time-viscosity curve slope of less than 200 Pa·s/minute for at least 5 minutes after achieving a viscosity of 500 Pa·s. The bone cement further can be characterized by a post-mixing time-viscosity curve slope of less than 100 Pa·s/minute for at least 15 minutes, 16 minutes, 17 minutes, 18 minutes, 19 minutes and 20 minutes.

In one embodiment, the bone cement comprises a first monomer-carrying component and a second polymer-carrying component, wherein post-mixing the mixture is characterized by a time-viscosity curve slope of less than 100 Pa·s/minute until to the mixture achieving a viscosity of 500 Pa·s. The bone cement post-mixing can be characterized by a time-viscosity curve slope of less than 100 Pa·s/minute immediately before the mixture achieves a viscosity of 800 Pa·s. The bone cement further can be characterized by a time-viscosity curve slope of less than 100 Pa·s/minute immediately before the mixture achieves a viscosity of 1000 Pa·s. The bone cement further can be characterized by a time-viscosity curve slope of less than 100 Pa·s/minute immediately before the mixture achieves a viscosity of 1500 Pa·s. The bone cement further can be characterized by a time-viscosity curve slope of less than 200 Pa·s/minute immediately before the mixture achieves a viscosity of 500 Pa·s. The bone cement further can be characterized by a time-viscosity curve slope of less than 200 Pa·s/minute immediately before the mixture achieves a viscosity of 1000 Pa·s. The bone cement further can be characterized by a time-viscosity curve slope of less than 200 Pa·s/minute immediately before the mixture achieves a viscosity of 1500 Pa·s. The bone cement further can be characterized by a time-viscosity curve slope of less than 200 Pa·s/minute immediately before the mixture achieves a viscosity of 2000 Pa·s.

In one embodiment, the bone cement comprises a first monomer-carrying component and a second polymer-carrying component, wherein post-mixing the mixture is characterized by a time-viscosity curve having a rate of change of less than 20% or less that 40% over an interval of at least 5 minutes, 10 minutes, 15 minutes and 20 minutes.

In one embodiment, the bone cement comprises a first monomer-carrying component and a second polymer-carrying component, wherein post-mixing the mixture of the first and second components is characterized as having a viscosity of less than 100 Pa·s at 10 minutes post-mixing, or less than 200 Pa·s at 15 minutes post-mixing, or less than 500 Pa·s at 18 minutes post-mixing.

In another embodiment, the bone cement formulation described above comprises first and second cement precursors, wherein the mixture is characterized by a post-mixing interval in which viscosity is between 500 Pa·s and 5000 Pa·s, and in which the change of viscosity of less than 30%/minute.

In another aspect and embodiment, the settable bone cement comprises first and second cement precursors, wherein the mixture is characterized by a post-mixing interval in which viscosity is between 500 Pa·s and 2000 Pa·s, and in which the change of viscosity of less than 20%/minute.

In another embodiment, the settable bone cement comprises a first monomer-carrying component and a second polymer-carrying component, wherein post-mixing the mixture is characterized by a change of viscosity of less than 20%/minute for at least three minutes after reaching 500 Pa·s, 1000 Pa·s, 1500 Pa·s and 2000 Pa·s. In another embodiment, the cement comprises a first monomer-carrying component and a second polymer-carrying component, wherein post-mixing the mixture is characterized by a change of viscosity of less than 30%/minute for at least three minutes after reaching 500 Pa·s, 1000 Pa·s, 1500 Pa·s and 2000 Pa·s. In a related embodiment, the cement comprises a first monomer-carrying component and a second polymer-carrying component, wherein post-mixing the mixture is characterized by a change of viscosity of less than 40%/minute for at least three minutes after reaching 500 Pa·s, 1000 Pa·s, 1500 Pa·s and 2000 Pa·s. In a related embodiment, the cement comprises a first monomer-carrying component and a second polymer-carrying component, wherein post-mixing the mixture is characterized by a change of viscosity of less than 30%/minute for at least five minutes after reaching 1000 Pa·s, 1500 Pa·s, 2000 Pa·s, 2500 Pa·s, 3000 Pa·s, 3500 Pa·s and 4000 Pa·s. In another related embodiment, the cement comprises a first monomer-carrying component and a second polymer-carrying component, wherein post-mixing the mixture is characterized by a change of viscosity of less than 40%/minute for at least five minutes after reaching 1000 Pa·s, 1500 Pa·s, 2000 Pa·s, 2500 Pa·s, 3000 Pa·s, 3500 Pa·s and 4000 Pa·s. In a related embodiment, the cement comprises a first monomer-carrying component and a second polymer-carrying component, wherein post-mixing the mixture is characterized by a change of viscosity of less than 50%/minute for at least five minutes after reaching 1000 Pa·s, 1500 Pa·s, 2000 Pa·s, 2500 Pa·s, 3000 Pa·s, 3500 Pa·s and 4000 Pa·s.

In another embodiment, a cement comprises a first monomer-carrying component and a second polymer-carrying component, wherein the mixture is characterized by a rate of change of viscosity of less than 50%/minute after achieving a viscosity of 5000 Pa·s. In a related embodiment, a cement comprises a first monomer-carrying component and a second polymer-carrying component, wherein the mixture is characterized by a rate of change of viscosity of less than 50%/minute after achieving a viscosity of 4000 Pa·s. In a related aspect, a cement comprises a first monomer-carrying component and a second polymer-carrying component, wherein the mixture is characterized by a rate of change of viscosity of less than 50%/minute after achieving a viscosity of 3000 Pa·s.

In another embodiment, a cement comprises a first monomer-carrying component and a second polymer-carrying component, wherein post-mixing the mixture is characterized by a rate of change of viscosity of less than 50%/minute for an interval preceding the point in time the mixture achieves 5000 Pa·s, the interval being at least 2 minutes, 3 minutes, 4 minutes, 5 minutes, 6 minutes and 8 minutes. In a related aspect, a cement comprises a first monomer-carrying component and a second polymer-carrying component, wherein post-mixing the mixture is characterized by a rate of change of viscosity of less than 40%/minute for an interval preceding the point in time the mixture achieves 5000 Pa·s, the interval being at least 2 minutes, 3 minutes, 4 minutes, 5 minutes, 6 minutes and 8 minutes. In a related aspect, a cement comprises a first monomer-carrying component and a second polymer-carrying component, wherein post-mixing the mixture is characterized by a rate of change of viscosity of less than 30%/minute for an interval preceding the point in time the mixture achieves 5000 Pa·s, the interval being at least 2 minutes, 3 minutes, 4 minutes, 5 minutes, 6 minutes and 8 minutes.

In another embodiment, a cement comprises a first monomer-carrying component and a second polymer-carrying component, wherein the mixture is characterized by a post-mixing interval of at least 4 minutes, 6 minutes, 8 minutes or 10 minutes in the interval preceding the point in time the mixture achieves 3000 Pa·s. In a related aspect, a cement comprises a first monomer-carrying component and a second polymer-carrying component, wherein the mixture is characterized by a post-mixing interval of at least 4 minutes, 6 minutes, 8 minutes or 10 minutes in the interval preceding the point in time the mixture achieves 4000 Pa·s. In a related aspect, a cement comprises a first monomer-carrying component and a second polymer-carrying component, wherein the mixture is characterized by a post-mixing interval of at least 4 minutes, 6 minutes, 8 minutes or 10 minutes in the interval preceding the point in time the mixture achieves 5000 Pa·s.

In another embodiment, a settable or curable bone cement is provided that comprises two mixable components as described above: a liquid monomer component and a non-liquid component. In this embodiment of bone cement, the non-liquid component includes polymer beads or particles, wherein this non-liquid component is configured for controlled differential BPO exposure to the liquid monomer over a setting interval of the bone cement. The controlled exposure of BPO will thus control the time-viscosity curve of cement injected into a bone.

In one embodiment of bone cement, the desired differential BPO exposure over the working time of the cement is provided by differing beads or particles and having differing BPO configurations therein. For example, the first beads of a first portion of the total volume can have a small diameter with a higher density of BPO when compared to second beads of a second portion of the total non-liquid component of the cement. The first portion of beads can have an average cross section of less than 100 microns, 80 microns, 60 microns or 40 microns. The first portion can have greater than 0.5 wt. % of BPO. The second volume of beads or particles can have an average cross section of greater than 40 microns, 60 microns, 80 microns and 100 microns, with a less than 0.5 wt. % of BPO. In combination, the volume of the first and second portions or volumes can have less than a 5.0 wt. % of BPO.

In another embodiment of bone cement, the BPO configuration in the non-liquid component can comprise particles of BPO and particles of a polymeric material alone or particles with an integrated BPO. In another embodiment, the polymer particles can have different regions of different BPO densities.

In another embodiment of bone cement, the BPO configuration in the non-liquid component can comprise particles having a surface coating of BPO. The BPO configuration can also comprise particles having BPO layers.

In one aspect of a method of utilizing a bone cement, the bone cement precursors are provided wherein the BPO configuration controls the initiation or the rate of chemical reaction caused by mixing the liquid monomer component and the non-liquid component. Thus, a method comprises mixing the liquid and non-liquid components, and injecting the bone cement into bone wherein the controlled BPO exposure provides a lengthened setting interval in which the mixture is configured for a flowability property that prevents unwanted extravasation. The method can provide a mixture that is configured to have a viscosity within 30 seconds post-mixing of at least 500 Pa·s, 1000 Pa·s, 1500 Pa·s and 2000 Pa·s. The method can provide a mixture that is configured for having a viscosity within 60 seconds post-mixing of at least 500 Pa·s, 1000 Pa·s, 1500 Pa·s, 2000 Pa·s and 2500 Pa·s. The method can provide a mixture that is configured for having a viscosity within 90 seconds post-mixing of at least 500 Pa·s, 1000 Pa·s, 1500 Pa·s, 2000 Pa·s and 3000 Pa·s.

In another aspect of a method of utilizing a bone cement, the bone cement precursors provide a mixture configured to have a viscosity after of less than 4000 Pa·s after 20 minutes post-mixing, after 18 minutes post-mixing, after 16 minutes post-mixing, after 14 minutes post-mixing and after 12 minutes post-mixing. In another aspect of a method, the mixture is configured to have a viscosity after of less than 3000 Pa·s after 20 minutes post-mixing, after 18 minutes post-mixing, after 16 minutes post-mixing, after 14 minutes post-mixing and after 12 minutes post-mixing. In another aspect of a method, the mixture is configured to have a viscosity of less than 2000 Pa·s after 20 minutes post-mixing, after 18 minutes post-mixing, after 16 minutes post-mixing, after 14 minutes post-mixing and after 12 minutes post-mixing.

In another embodiment, the bone cement comprises a monomer component and polymer component, wherein the polymer component includes a first volume of beads having a first average wt. % of BPO on the basis of the total weight of the first volume and a second volume of beads having a second average wt. % of BPO on the basis of the total weight of the second volume. The beads of the first volume of beads can have an average cross section of less than 100 microns, 80 microns, 60 microns or 40 microns. The beads of the second volume of beads can have an average cross section of greater than 40 microns, 60 microns, 80 microns and 100 microns. In some bone cement embodiments, the first volume has less than 0.5 wt. % of BPO and the second volume has greater than 0.5 wt. % of BPO. Embodiments of bone cement may have combined first and second volumes having less than a 5.0 wt. % of BPO or less than a 2.5 wt. % of BPO. In some bone cement embodiments, the combined first and second volumes have greater than a 0.5 wt. % of BPO or greater than a 1.0 wt. % of BPO. In other embodiments, at least a portion of the first volume is without BPO or at least a portion of the second volume is without BPO.

In another embodiment, the bone cement comprises a monomer component and polymer component, wherein the polymer component comprises a volume of beads carrying from 0.2% and 0.6% of BPO on the basis of the total weight of the volume, wherein at least 80% of the BPO is carried on a sub-volume of beads, the beads having a mean cross section of greater than 100 microns, and wherein less than 20% of the BPO is carried on a sub-volume of beads, the beads having a mean cross section of less than 100 microns.

In another embodiment, the bone cement comprises a monomer component and polymer component, wherein the polymer component comprises a volume of beads carrying from 0.2% and 0.6% of BPO on the basis of the total weight of the volume, wherein 100% of the BPO is carried on a portion of the bead volume where the beads have a mean cross section of greater than 100 microns, and wherein no BPO is carried on a portion of the bead volume where the beads have a mean cross section of less than 100 microns.

In another embodiment, the bone cement comprises a monomer component and polymer component, wherein the polymer component comprises a volume of beads of at least one polymeric material, wherein the polymer component carries from 0.2% and 3.0% BPO on the basis of the total weight of the volume, wherein a first portion of the bead volume carries BPO in a surface coating and wherein a second portion of the bead volume carries BPO intermixed in the at least one polymeric material.

In another embodiment, the bone cement comprises a monomer component and polymer component, wherein the polymer component comprises a volume of beads of at least one polymeric material and from 0.2% and 3.0% BPO on the basis of the total weight of the volume, and wherein the BPO is provided in at least two of the following forms: as a surface coating on beads, as BPO particles, as BPO in microcapsules, as BPO particles within beads of a polymeric material, and as BPO in microcapsules within beads of a polymeric material.

In some methods, a bone cement is provided comprising a mixture of a liquid monomer component and polymer component of particles which includes distributing BPO within the mixture to provide a selected BPO availability to be wetted by the monomer component over first and second intervals, wherein the BPO availability per second over the first interval is substantially greater than the BPO availability per second over the second interval. Thereafter, the liquid monomer component and polymer component are mixed and then injected into bone. In this method, the selected BPO availability is provided by at least two different particles having differing BPO configurations therein. In one embodiment, the selected BPO availability is provided by a differential BPO exposure in a surface area of the particles. In another embodiment, the selected BPO exposure is provided in part by particles having a mixed polymeric material and BPO. In another embodiment, the selected BPO exposure is provided in part by particles having a surface coating of BPO. In another embodiment, the selected BPO exposure is provided in part by microencapsulated BPO. In yet another embodiment, the selected BPO exposure is provided by particles having layers of polymeric materials and BPO.

Figure 4:
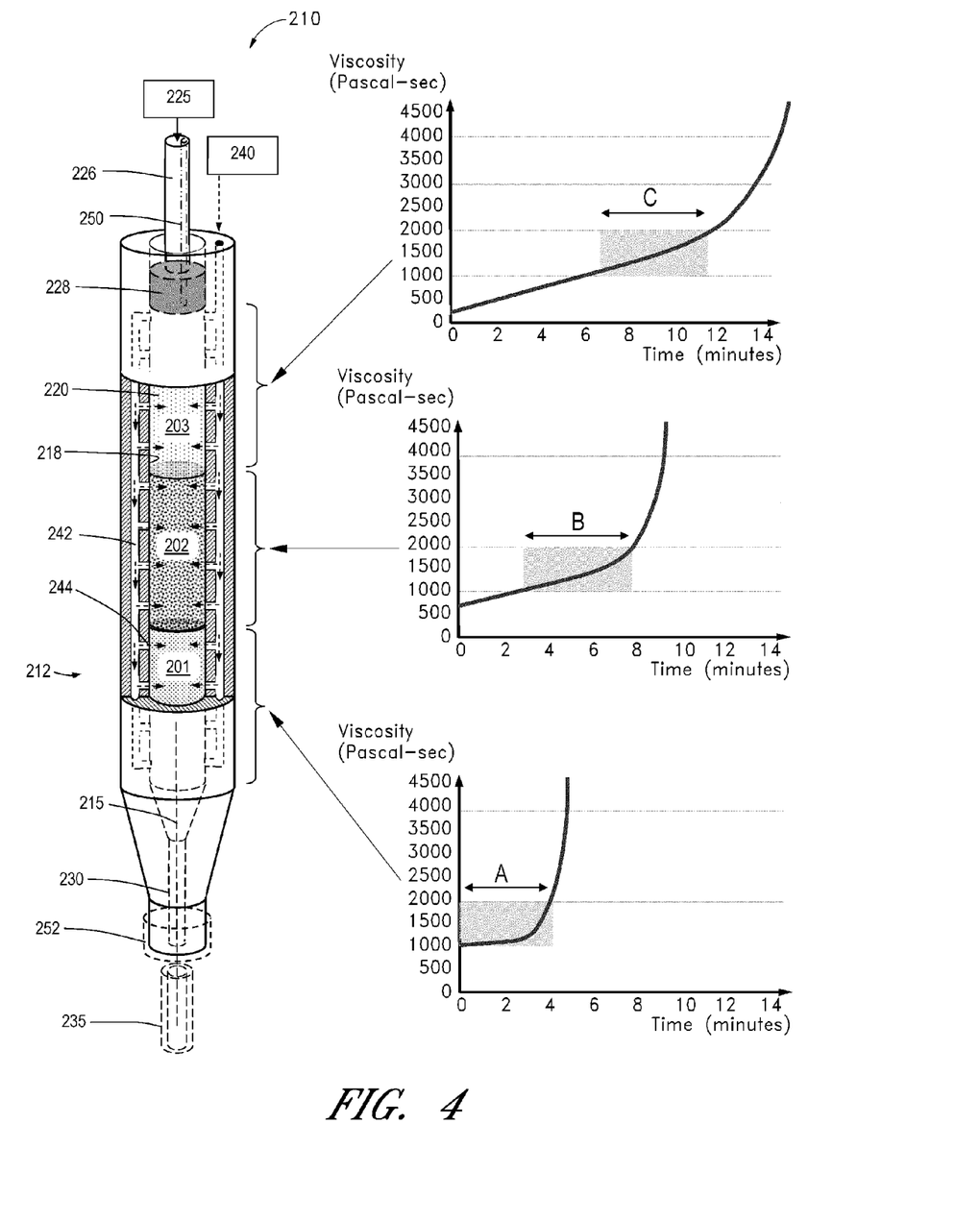
FIG. 4 is a cut-away schematic view of another embodiment of a bone cement injection system.

FIG. 4 illustrates another embodiment of a biomaterial injection system 210 that comprises a syringe-like body 212 having an axis 215 with an interior chamber 218 carrying a volume (e.g., column) 220 of biomaterial therein. As can be seen in FIG. 4, the column of biomaterial can consist of volume or column portions of the PMMA bone cements 201, 202 and 203 that are configured to be injected, e.g., serially, into a bone such as a vertebral body. A drive system 225 for driving the cement comprises a driving shaft 226 with a plunger head or element 228 with an o-ring or other seal-type element that allows for pushing the column 220 of biomaterial distally in chamber 218. The bone cement volume can be pushed through chamber 218 and flow channel 230 into any injector needle or cannula 235 that has a cooperating flow channel therein. The cannula 235 can be made of any suitable metal or plastic sleeve and can be detachably coupleable to body 212 and can extend to one or more flow outlets. The driving shaft 226 can be a manually advanced plunger assembly, or any type of hydraulic system, CO2 gas cartridge system, pneumatic system, cable drive system, screw drive system, a spring system or other pump system (indicated at 225), any of which can be computer controlled with a microprocessor that executes one or more control algorithms.

FIG. 4 further illustrates a monomer infusion system of the invention which comprises a liquid monomer source 240 that is detachably coupleable to at least one infusion channel 242 in body 212 that communicates with chamber 218. In one embodiment, the infusion channel comprises a plurality of ports 244 over the length and about the circumference of the chamber to allow rapid, uniform monomer wetting of the column of biomaterial. The arrows in the channel(s) 242 and port(s) 244 indicate a flow of monomer into the biomaterial. In order to drive the liquid monomer into the column 220 to cause rapid wetting, the pressure of the monomer inflow can be greater that 1 psi, 5 psi, 10 psi, 50 psi or 100 psi. In one embodiment, the chamber 218 or cement column 220 has a small cross sectional diameter that allows for rapid monomer diffusion, for example less than 20 mm, 15 mm or 10 mm. In order to diffuse the monomer within the polymer beads of the column, at least one vent can be used to vent air from the column that is displaced by the liquid monomer. In one embodiment shown in FIG. 4, a vent channel 250 is shown in the shaft 226 but it should be appreciated that there can be one or more vents with optional check valves in the shaft 226, the body 212 or a removable cap 252 at the distal end of the body 212.

The above description is intended to be illustrative and not exhaustive. In addition, particular characteristics, features, dimensions and the like are presented in the dependent claims. These can be combined in various embodiments and fall within the scope of the disclosure. It should also be understood that various additional embodiments encompass the dependent claims as if they were alternatively written in a multiple dependent claim format, including reference to other independent claims. Specific characteristics and features of the embodiments of the systems and methods are described in relation to some figures and not in others, and this is for convenience only. While certain principles have been made clear in the exemplary descriptions and combinations, it will be obvious to those skilled in the art that modifications may be utilized in practice, which are particularly adapted to specific environments and operative requirements without departing from the principles espoused herein.

Of course, the foregoing description is that of certain features, aspects and advantages, to which various changes and modifications can be made without departing from the spirit and scope of the disclosure. Moreover, the bone treatment systems and methods need not feature all of the objects, advantages, features and aspects discussed above. Thus, for example, those skill in the art will recognize that the systems can be embodied or carried out in a manner that achieves or optimizes one advantage or a group of advantages as taught herein without necessarily achieving other objects or advantages as may be taught or suggested herein. In addition, while a number of variations have been shown and described in detail, other modifications and methods of use, which are within the scope of the disclosure, will be readily apparent to those of skill in the art based upon this disclosure. It is contemplated that various combinations or sub-combinations of these specific features and aspects of embodiments may be made and still fall within the scope of the disclosure. Accordingly, it should be understood that various features and aspects of the disclosed embodiments can be combined with or substituted for one another in order to form varying modes of the discussed bone treatment systems and methods.

What is claimed is:

1. A bone cement injection system, comprising:
an elongate structure with an interior space and having a first opening at a proximal end and a second opening at a distal end of the elongate structure, a single section of the interior space containing a column of a non-liquid polymer component of a curable bone cement, wherein the column includes a plurality of discrete predetermined column portions of different non-liquid polymer component formulations arranged sequentially within the single section of the interior space;
a container coupleable to the proximal end of the elongate structure and containing a liquid monomer component of the curable bone cement therein; and a negative pressure mechanism coupleable to the distal end of the elongate structure, the negative pressure mechanism configured to draw the liquid monomer component from the container and through the first opening at the proximal end of the elongate structure into the interior space to saturate the plurality of discrete predetermined column portions of different non-liquid polymer component formulations, where each of the saturated column portions of different non-liquid polymer component formulations has a different bone cement time-viscosity characteristic.

2. The bone cement injection system of claim 1, wherein the container comprises a funnel member configured for coupling to the elongate structure for receiving the liquid monomer component.

3. The bone cement injection system of claim 1, further comprising a force-application system coupleable to the elongate structure and configured to push the saturated column portions of different non-liquid polymer component formulations of the bone cement from the elongate structure through the second opening at the distal end.

4. The bone cement injection system of claim 3, further comprising a manual actuator for controlling a rate of actuating the force-application system to inject the column of biomaterial into a bone.

5. The bone cement injection system of claim 3, further comprising a computer controller for controlling the force-application system to control a rate of injecting the saturated column portions of different non-liquid polymer component formulations of the bone cement into bone.

6. The bone cement injection system of claim 5, wherein the controller is configured for injecting the saturated column portions of different non-liquid polymer component formulations of the bone cement at the rate of between 0.5 cc and 5 cc per minute.

7. The bone cement injection system of claim 1, wherein the predetermined column portions are positioned axially within the column of non-liquid polymer component of a curable bone cement.

8. The bone cement injection system of claim 1, wherein the predetermined column portions are positioned concentrically within the column of non-liquid polymer component of a curable bone cement.

9. The bone cement injection system of claim 1, further comprising a sensor system that provides a signal of a parameter of the bone cement by at least one of visual, aural or tactile signals.

10. The bone cement injection system of claim 9, wherein the sensor system includes at least one of a temperature sensor, a flow sensor, an electrical parameter sensor, an ultrasound sensor, and a thermochromic material.

11. The system of claim 1, wherein the negative pressure mechanism is configured to draw the liquid monomer component into the interior space of the elongate structure such that the liquid monomer component wets the plurality of discrete predetermined column portions of different non-liquid polymer component formulations uniformly.

12. A bone cement injection system comprises:
a container body with an interior chamber;
a plurality of volumes of different non-liquid polymer powder components of a two-part curable bone cement disposed sequentially within a single section of the interior chamber, each of the different non-liquid polymer powder components having a different formulation;
a liquid monomer component
a negative pressure source detachably coupled to a distal portion of the container body and configured to apply negative pressure to draw the liquid monomer component of the two-part curable bone cement into the interior chamber through an opening at a proximal portion of the container body and through the volumes of different non-liquid polymer powder components disposed within the interior chamber, where the monomer saturates each volume of polymer powder component so to form the bone cement, wherein each of the saturated volumes of different non-liquid polymer powder components has a different bone cement time viscosity characteristic.

13. The system of claim 12, wherein the plurality of different non-liquid polymer powder components are each in different axial portions of a biomaterial column in the interior chamber of the container body.

14. The system of claim 13, wherein the plurality of different non-liquid polymer powder components comprise three different specialized formulations of the non-liquid polymer powder component of two-part curable bone cement.

15. The system of claim 12, wherein each of the plurality of different non-liquid polymer powder components have at least one of different levels of initiator, different levels of activator, and different mean dimensions of polymer particles as compared to another one of the plurality of different non-liquid polymer powder components.

16. The system of claim 12, wherein the container body comprises a syringe body.

17. The system of claim 16, wherein the syringe body has a fitting at the proximal portion for connecting a pressurization mechanism to eject bone cement from the syringe body.

18. The system of claim 12, wherein the negative pressure source comprises a syringe with a lockable plunger assembly slidable within the syringe to apply suction to the container body.

19. The system of claim 18, further comprising a filter intermediate the container body and the negative pressure source.

20. The system of claim 12, wherein the negative pressure source is configured to draw the liquid monomer component into the interior chamber of the container body such that the liquid monomer component wets the plurality of different non-liquid polymer component formulations uniformly.

21. A bone cement injection system, comprising:
a syringe body having an internal chamber, a distal opening and a proximal opening;
a liquid monomer component of a two-part curable bone cement;
a plurality of discrete and different volumes of a non-liquid polymer powder component of the two-part curable bone cement positioned sequentially along a longitudinal axis of the syringe body within a single section of the internal chamber, each of the different volumes of non-liquid polymer powder components having a different formulation, where when mixed with the liquid monomer component each of the plurality of discrete and different volumes of non-liquid polymer powder components are configured to polymerize and form a bone cement within the syringe body, wherein post-mixing each of the plurality of discrete and different volumes of non-liquid polymer powder components has a different bone cement time viscosity characteristic;
wherein the proximal opening is configured to receive the liquid monomer component for mixing with the plurality of discrete and different non-liquid polymer powder components, and the distal end of the syringe body is configured to eject bone cement from the syringe body.

22. The bone cement injection system of claim 21, wherein a proximal end of the syringe body comprises a threaded fitting configured to releasably couple the syringe body to a pressurization mechanism configured to apply a force on the bone cement to eject bone cement from the distal opening of the syringe body.

23. The bone cement injection system of claim 21, wherein the plurality of discrete and different non-liquid polymer powder components form bone cement with different post-saturation time intervals of polymerization.

24. The bone cement injection system of claim 23, wherein a distal most non-liquid polymer powder component has a shorter post-saturation time interval of polymerization than a proximal most non-liquid polymer powder component.

* * * * *

UNITED STATES PATENT AND TRADEMARK OFFICE
CERTIFICATE OF CORRECTION

PATENT NO.        : 8,562,620 B2                              Page 1 of 1
APPLICATION NO.   : 12/427531
DATED             : October 22, 2013
INVENTOR(S)       : Truckai et al.

It is certified that error appears in the above-identified patent and that said Letters Patent is hereby corrected as shown below:

In the Claims:

In column 20 at line 7, In Claim 12, change "so" to -- so as --.

Signed and Sealed this
Sixth Day of May, 2014

Michelle K. Lee
*Deputy Director of the United States Patent and Trademark Office*